United States Patent
Yang et al.

(10) Patent No.: US 10,264,952 B2
(45) Date of Patent: Apr. 23, 2019

(54) METHOD FOR POSITIONING ENDOSCOPE AND AUXILIARY POSITIONING DEVICE FOR SAME METHOD

(71) Applicant: HIWIN TECHNOLOGIES CORP., Taichung (TW)

(72) Inventors: Hung-Ju Yang, Taichung (TW); Kun-Jia Hsu, Taichung (TW); Ren-Jeng Wang, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 696 days.

(21) Appl. No.: 14/667,176

(22) Filed: Mar. 24, 2015

(65) Prior Publication Data

US 2016/0278618 A1    Sep. 29, 2016

(51) Int. Cl.
*A61B 1/00* (2006.01)
*A61M 13/00* (2006.01)
*A61B 34/30* (2016.01)
*A61B 18/00* (2006.01)

(52) U.S. Cl.
CPC ...... *A61B 1/00149* (2013.01); *A61B 1/00006* (2013.01); *A61B 2018/00172* (2013.01); *A61B 2034/301* (2016.02); *A61M 13/003* (2013.01); *Y10S 901/02* (2013.01)

(58) Field of Classification Search
CPC .............. A61B 1/00131; A61B 1/0014; A61B 1/00147; A61B 1/00149; A61B 90/50; A61B 34/30; B25J 18/007
See application file for complete search history.

(56) References Cited

U.S. PATENT DOCUMENTS

| 5,697,939 | A | 12/1997 | Kubota et al. | |
|---|---|---|---|---|
| 7,841,979 | B2* | 11/2010 | Hirose | A61B 1/00048 248/122.1 |
| 8,048,088 | B2* | 11/2011 | Green | B25J 3/04 606/1 |
| 8,374,677 | B2* | 2/2013 | Piferi | G01R 33/286 600/417 |
| 8,858,423 | B2* | 10/2014 | Yasunaga | A61B 1/00149 600/102 |

* cited by examiner

*Primary Examiner* — Alexandra L Newton

(74) *Attorney, Agent, or Firm* — Muncy, Geissler, Olds & Lowe, P.C.

(57) ABSTRACT

A method for positioning an endoscope involves installing an auxiliary positioning device on a robot arm, coinciding a terminal of a docking member of the auxiliary positioning device with a spherical remote center of motion defined by the robot arm, inserting and fixing the endoscope inside the auxiliary positioning device, removing the docking member of the auxiliary positioning device so that a terminal of the endoscope coincides with the spherical remote center of motion of the robot arm, and then inserting the endoscope into a body cavity catheter for finalizing positioning. Thereby, the method helps to save time used for preoperative preparation and provides more precise positioning, without using any additional positioning tools to approach the body cavity, thereby reducing the risk of infection.

4 Claims, 11 Drawing Sheets

METHOD FOR POSITIONING ENDOSCOPE AND AUXILIARY POSITIONING DEVICE FOR SAME METHOD

BACKGROUND OF THE INVENTION

1. Technical Field

The present invention relates to endoscopy, and more particularly to a method for positioning an endoscope and an auxiliary positioning device used in the method.

2. Description of Related Art

Before inserting an endoscope into a patient's body cavity, medical professionals have to first position a point of incision at the surface of the body cavity. Only after the point of incision is well positioned, the endoscope can be sent into the patient's body cavity through the point of incision. In the conventional positioning technology, as one described in U.S. Pat. No. 5,697,939, two abreast image-projecting devices are used to project images on the targeted body cavity and the site where the two images coincide is the point of incision. However, such a positioning process is time-consuming and unfavorable to medical treatment. In addition, since the surface of the body cavity is not flat and even, the projected images tend to have distortion and cause errors in positioning. Another known positioning method is to use a scale to determine the relative position between the virtual center of the robot arm and the point of incision on the body cavity. However, in use of the scale, the scale is unavoidably contacted with the surface of the body cavity, so the risk of infection at the cut is relatively high. This approach also has the problems related to undulation and unevenness of the surface of the body cavity, so errors may happen if the scale is not placed perfectly.

SUMMARY OF THE INVENTION

The primary objective of the present invention is to provide a method for positioning an endoscope, which helps to reduce time required by preoperative preparation and provide precise positioning, while reducing the risk of infection.

For achieving the foregoing objective, the disclosed method comprises five steps. First, a robot arm is installed. The robot arm defines a spherical remote center of motion. In the second step, an auxiliary positioning device is prepared. The auxiliary positioning device has a fastener, a detachably connected to the docking member of the fastener, and an apparatus-receiving hole passing through the fastener and the docking member. The fastener of the auxiliary positioning device is installed on the robot arm, so that the docking member the auxiliary positioning device has its terminal coinciding with the spherical remote center of motion of the robot arm. In the third step, an endoscope is inserted into the apparatus-receiving hole of the auxiliary positioning device, so that the terminal of the endoscope is aligned with the terminal of the docking member of the auxiliary positioning device. In the fourth step, the docking member of the auxiliary positioning device is removed, so that the terminal of the endoscope coincides with the spherical remote center of motion of the robot arm. In the fifth step, the endoscope is inserted into a catheter that has been inserted into a body cavity.

From the above steps it is learned that when the endoscope is inserted into the body cavity through the catheter, the positioning process is completed at the same time. In other words, the disclosed method can complete two works for preoperative preparation in a single action. In addition, since the entire process involves no additional tools that directly contact the patient's body cavity, the risk of infection can be significantly reduced.

Preferably, the auxiliary positioning device further has a knob provided on the fastener. When the endoscope has been inserted into the apparatus-receiving hole of the auxiliary positioning device, the knob can be rotated to make the fastener fix the endoscope.

Preferably, when the docking member of the auxiliary positioning device has been removed, a light source of the endoscope is turned on. After the endoscope is inserted into the body cavity through the catheter, by checking whether the light source is blocked by the body cavity, the position of the endoscope can be further confirmed.

Preferably, before the endoscope is inserted into the body cavity, a positioning depth where the endoscope is inserted into the body cavity is first selected. Then a movable seat drives the fastener of the auxiliary positioning device, so that the fastener and the endoscope move away from the spherical remote center of motion of the robot arm for predetermined distance. The predetermined distance is equal to the positioning depth. Then the endoscope is inserted into the catheter. After the insertion, the movable seat again drives the fastener of the auxiliary positioning device, so that the fastener and the endoscope move toward the spherical remote center of motion of the robot arm for the predetermined distance. At this time, the positioning process of the endoscope is completed.

Preferably, the present invention has another objective to provide an auxiliary positioning device as that used in the previously described method. The auxiliary positioning device has a fastener and a docking member. The fastener has a first through hole, and the docking member has a first end, a second end, and a second through hole running through the first and second ends. The second end is detachably connected to the fastener, and the second through hole is coaxially communicated with the first through hole of the fastener, so that the first and second through holes jointly form an apparatus-receiving hole, for the endoscope to be inserted thereto and in turn assisting the positioning process of the endoscope.

DETAILED DESCRIPTION OF THE INVENTION

Figure 1:
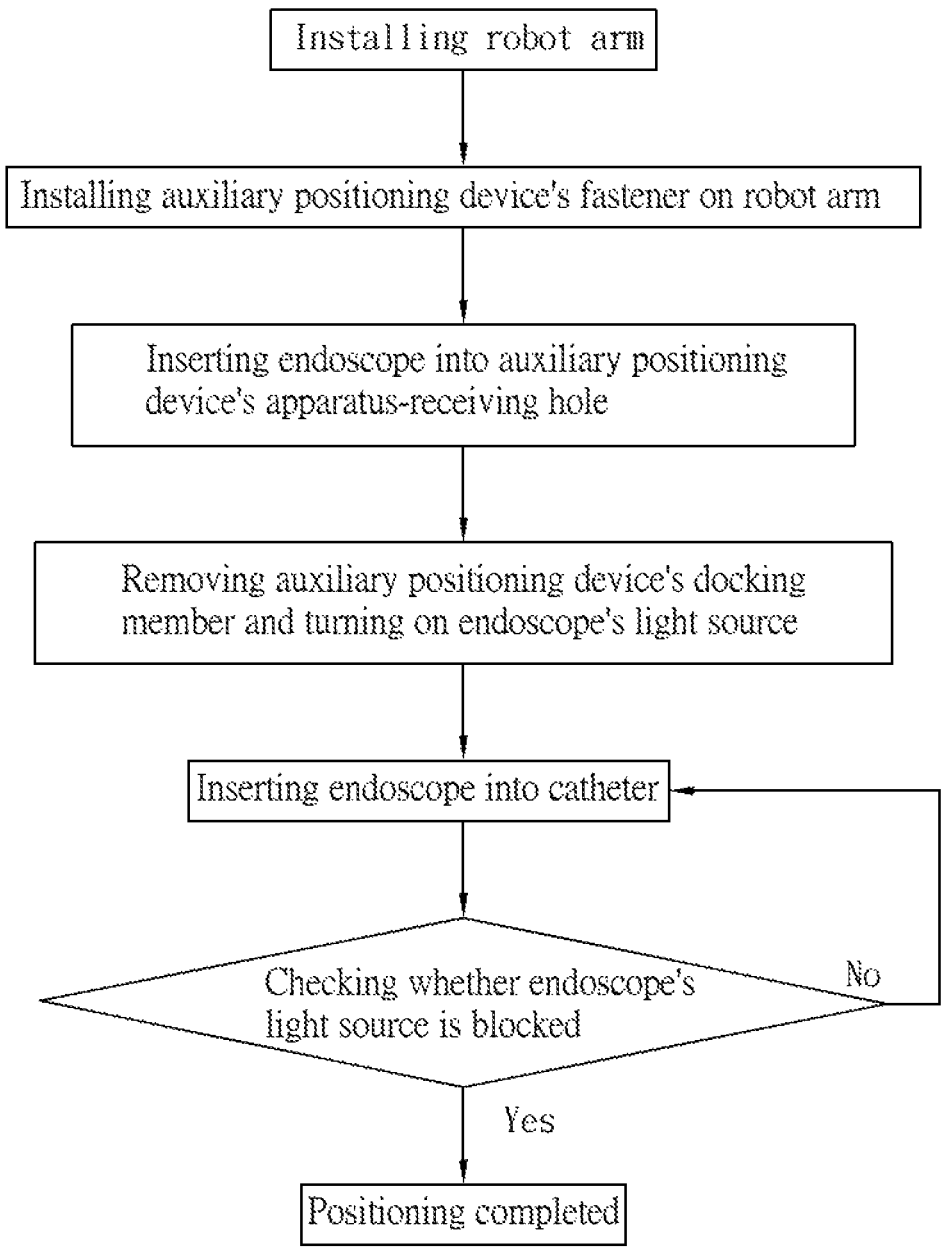
FIG. 1 is a block diagram of a first embodiment of the present invention.

Referring to FIG. 1, according to the first embodiment of the present invention, a positioning method comprises the following steps.

Figure 2:
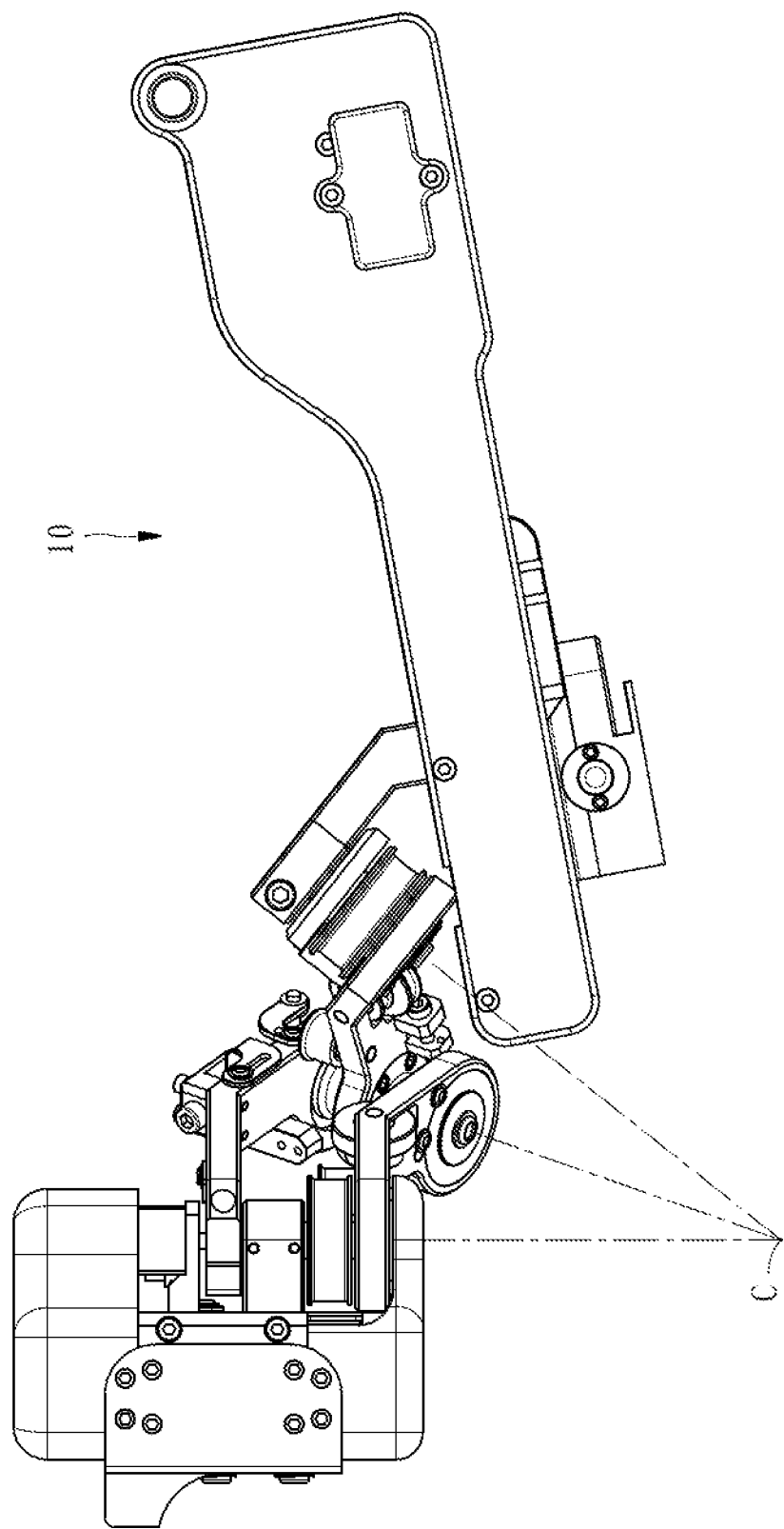
FIG. 2 is a plane view of a robot arm used in the present invention.

In Step a), a robot arm 10 is installed. As shown in FIG. 2, each of rotatable parts of the robot arm 10 has a revolving axis and all the revolving axes intersect at a spherical remote center of motion C. Thus, during operation, each of the rotatable parts is regarded as moving on a surface of an imaginary sphere cantered at the spherical remote center of motion C. The robot arm 10 used in the present invention is as one disclosed in Taiwan Patent Application No. 103102343 filed by the present inventor and the detailed description is thus omitted herein.

Figure 3:
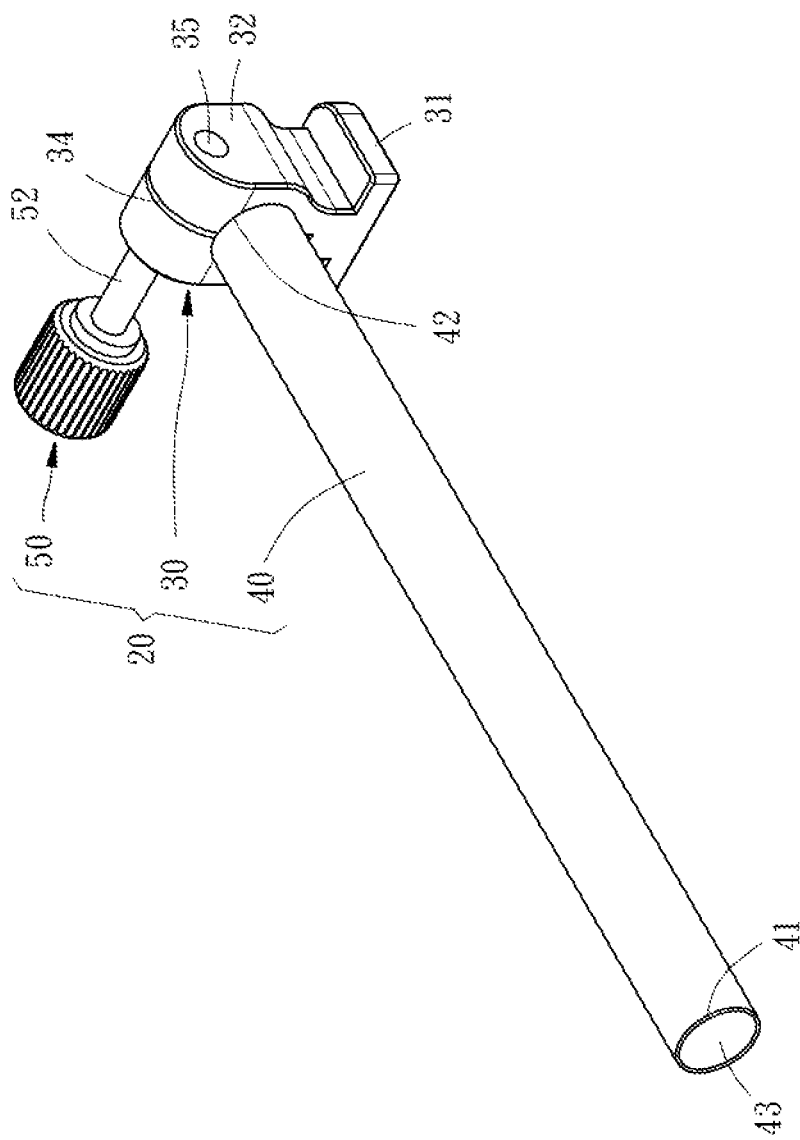
FIG. 3 is a perspective view of an auxiliary positioning device of the present invention.
Figure 4:
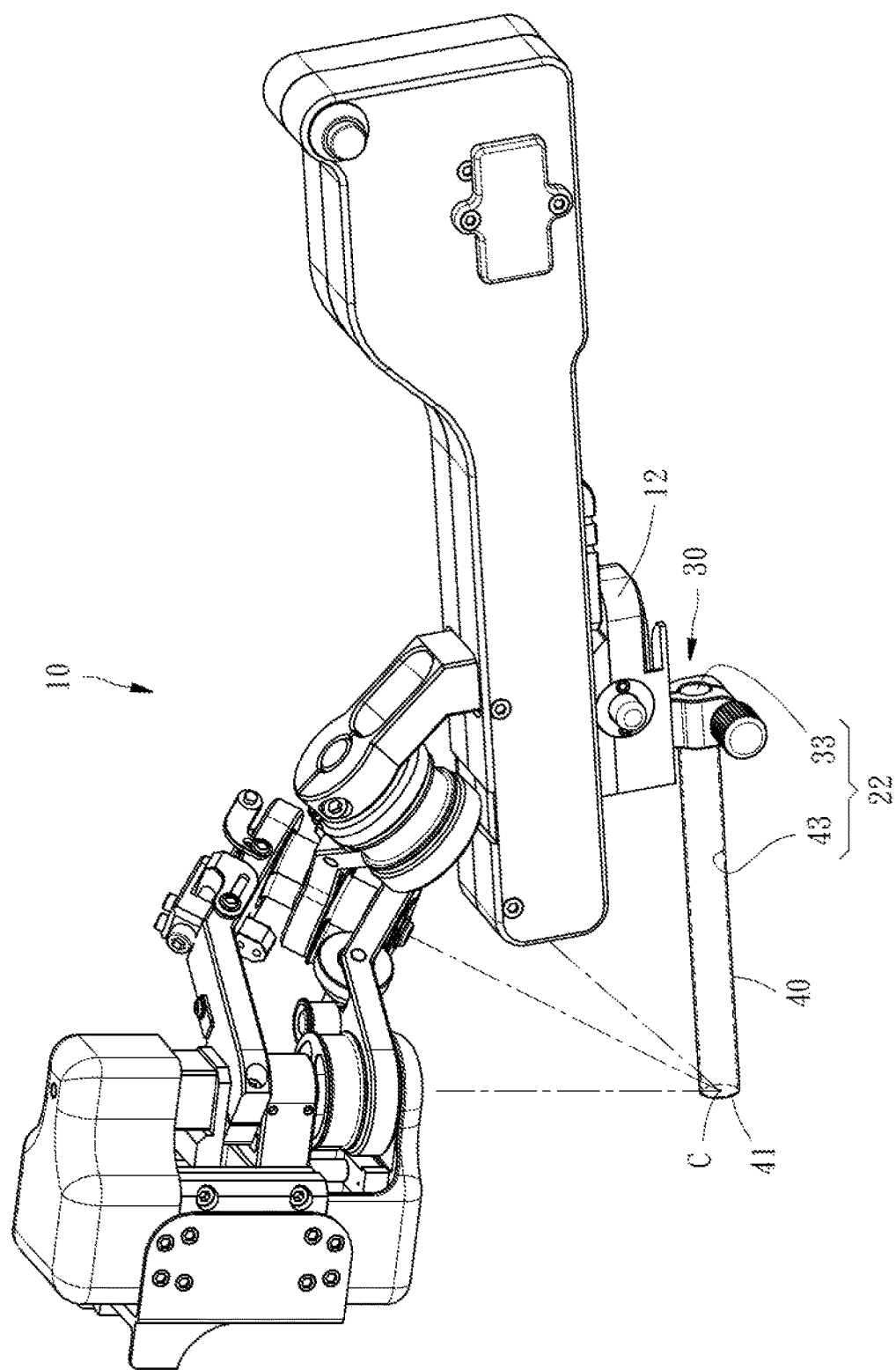
FIG. 4, similar to FIG. 2, shows the auxiliary positioning device installed on the robot arm.

In Step b), an auxiliary positioning device 20 is prepared. As shown in FIG. 3, the auxiliary positioning device 20 has a fastener 30, a docking member 40, and a knob 50. The fastener 30 has a fastening portion 31, a clamping portion 32 connected to the fastening portion 31, a first through hole 33 passing through the clamping portion 32 (as shown in FIG. 4), a slit 34 communicated with the first through hole 33, and a threaded hole 35 communicated with the slit 34. Additionally, the docking member 40 has a first end 41, a second end 42, and a second through hole 43 running between the first and second ends 41, 42. The second end 42 of the docking member 40 is detachably connected to (e.g. adhered to) the clamping portion 32 of the fastener 30, so that the second through hole 43 of the docking member 40 is axially communicated with and connected to the first through hole 33 of the fastener 30 (as shown in FIG. 4). Thereby, an apparatus-receiving hole 22 is formed by the first through hole 33 of the fastener 30 and the second through hole 43 of the docking member 40. The knob 50 has a screw 52, and is installed in threaded hole 35 of the fastener 30 by means of the screw 52, so that when the knob 50 is screwed to the end, the inner diameter of the first through hole 33 of the fastener 30 can be changed. When working with the robot arm 10, as shown in FIG. 4, the fastening portion 31 of the fastener 30 of the auxiliary positioning device 20 is installed on a movable seat 12 of the robot arm 10, so that the auxiliary positioning device 20 and the movable seat 12 of the robot arm 10 move synchronously. After installation, the first end 41 of the docking member 40 of the auxiliary positioning device 20 coincides with the remote center of motion C of the robot arm 10.

Figure 5:
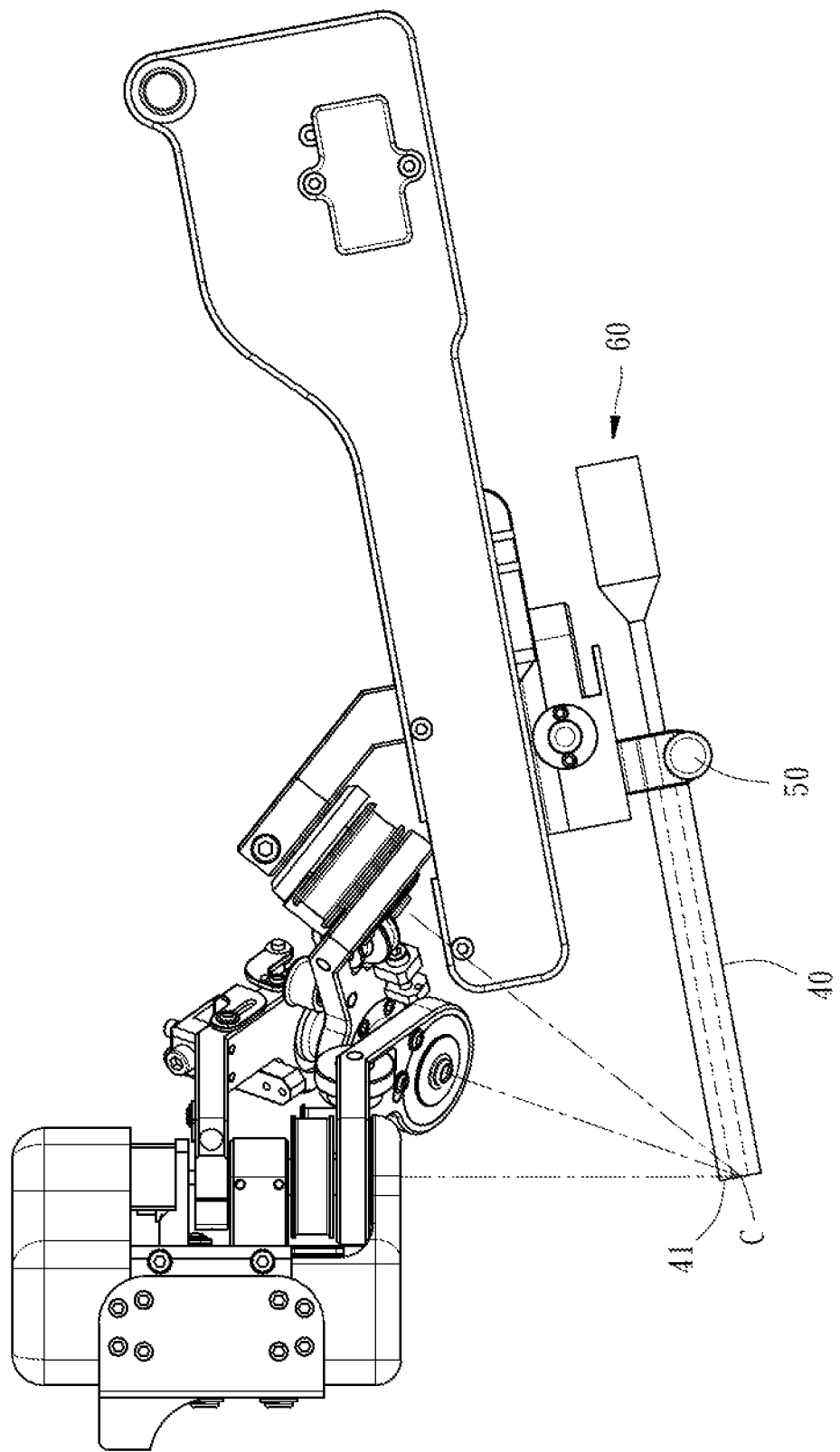
FIG. 5, similar to FIG. 4, shows an endoscope inserted into an apparatus-receiving hole of the auxiliary positioning device.

In Step c), as shown in FIG. 5, an endoscope 60 is inserted into the apparatus-receiving hole 22 of the auxiliary positioning device 20, so that the terminal of the endoscope 60 is aligned with the first end 41 of the docking member 40 of the auxiliary positioning device 20. Then the knob 50 is screwed to the end, so that the clamping portion 32 of the fastener 30 fixes the endoscope 60.

Figure 6:
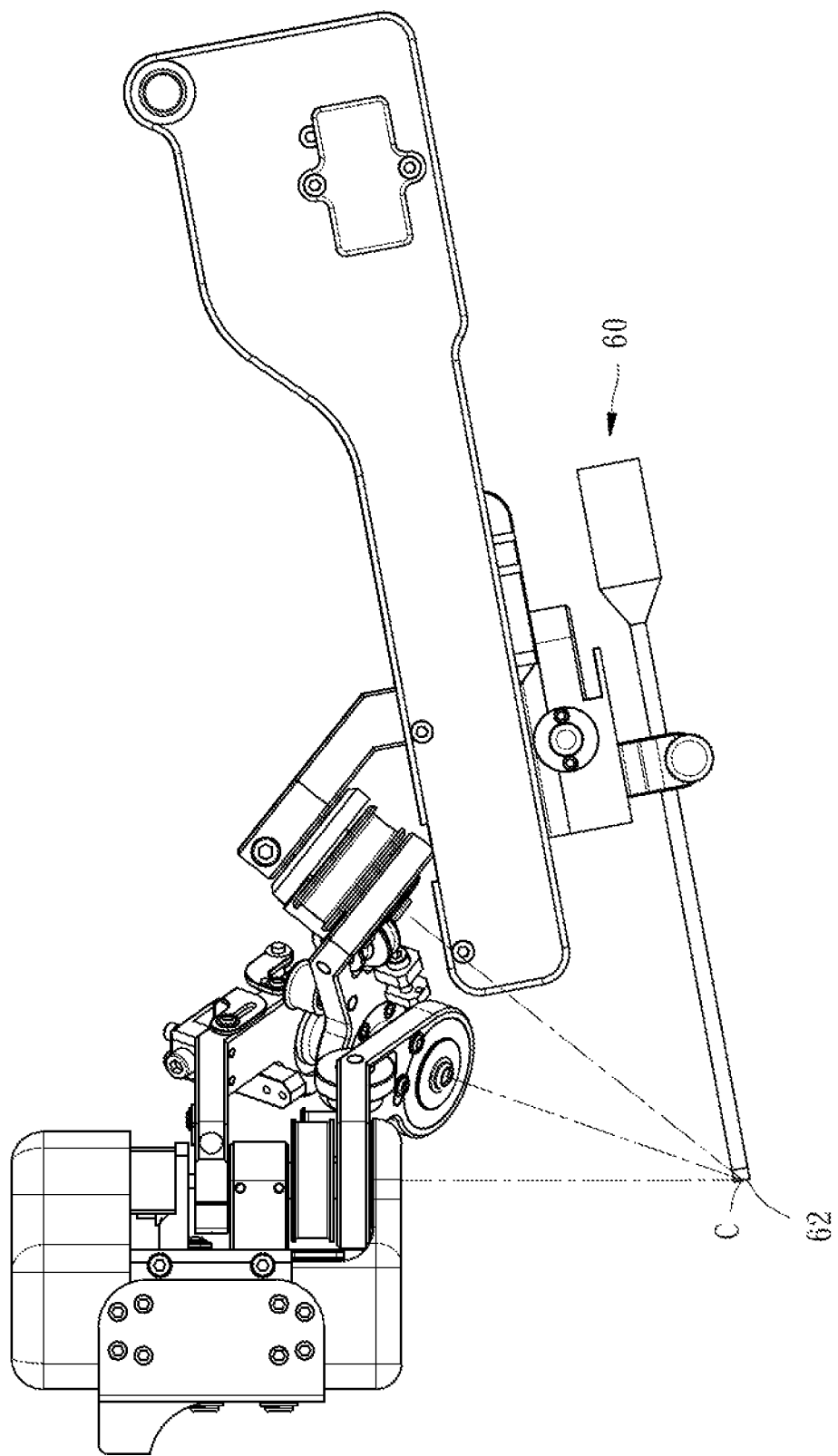
FIG. 6, similar to FIG. 5, shows the auxiliary positioning device with the docking member removed.

In Step d), as shown in FIG. 6, the docking member 40 of the auxiliary positioning device 20 is removed, so that the terminal of the endoscope 60 coincides with the spherical remote center of motion C of the robot arm 10. Then a light source 62 of the endoscope 60 is turned on.

Figure 7:
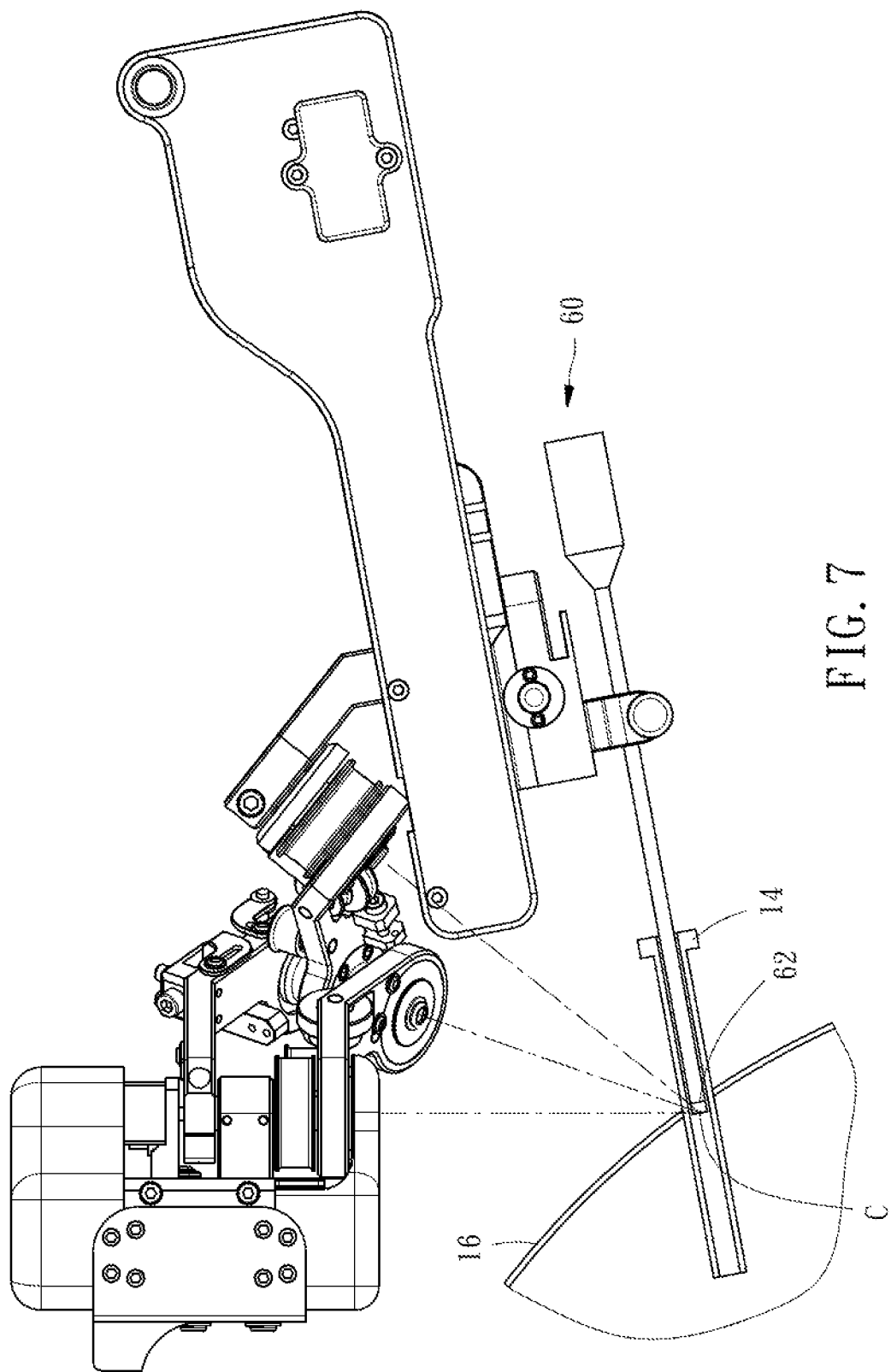
FIG. 7, similar to FIG. 6, shows a terminal of the endoscope entering a body cavity through a catheter.

In Step e), as shown in FIG. 7, the endoscope 60 is inserted into a catheter 14. The catheter 14 has been inserted into a patient's body cavity 16 right on the point of incision. While the endoscope 60 is inserted into the catheter 14, it is checked that whether the light source 62 of the endoscope 60 is blocked by the body cavity 16. When the light source 62 of the endoscope 60 is blocked by the body cavity 16, it is indicated that the spherical remote center of motion C of the robot arm 10 and the point of incision of the body cavity 16 have superposition, thereby accomplishing the positioning of the endoscope 60.

It is to be noted that, the foregoing steps are established on the assumption that the site where the endoscope 60 is to be inserted is right around the surface of the body cavity 16. In the event that the site where the endoscope 60 is to be inserted is away from the surface of the body cavity 16 for a depth, some more steps may be required to position the endoscope 60 properly.

Figure 8:
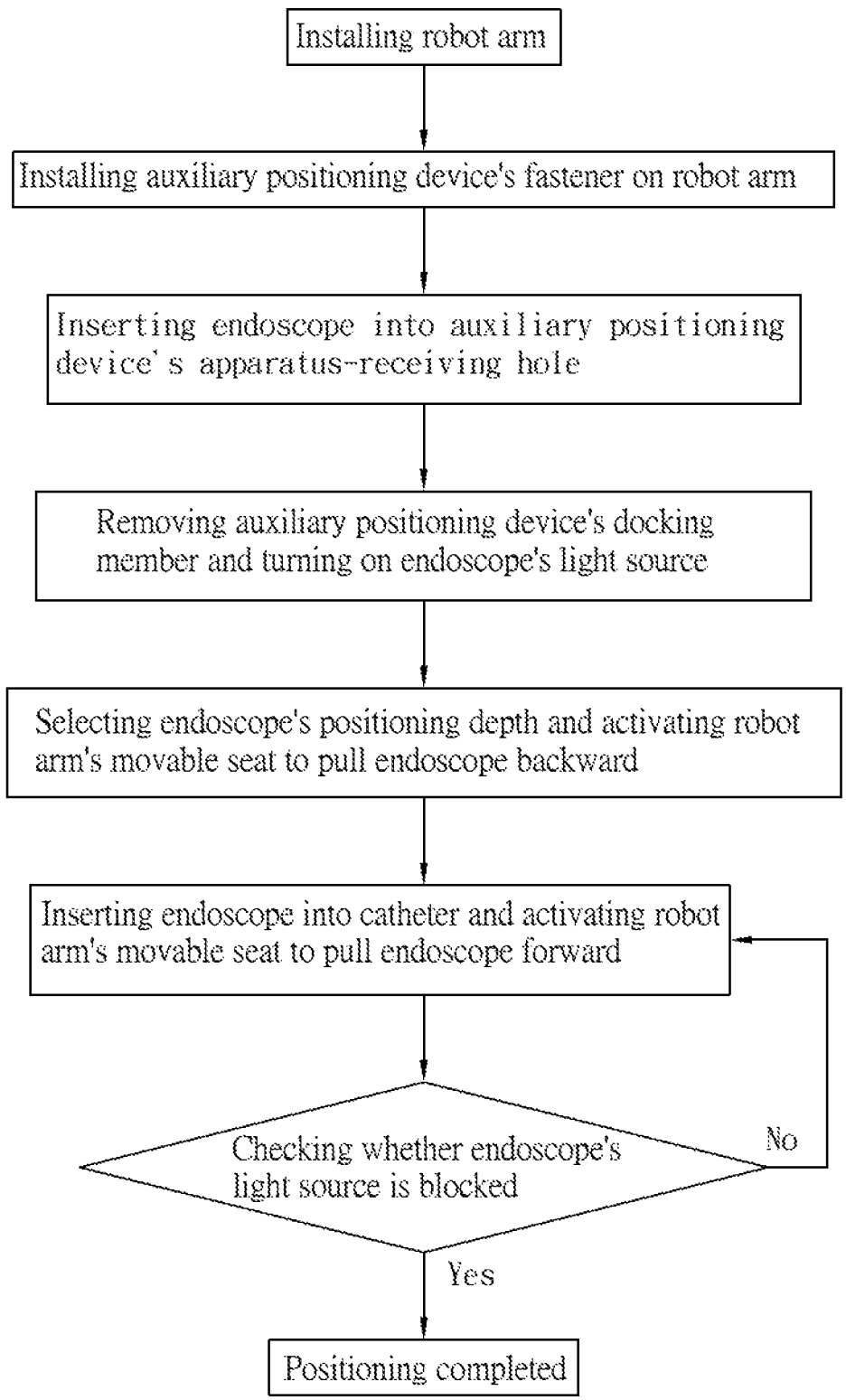
FIG. 8 is a block diagram of a second embodiment of the present invention.
Figure 9:
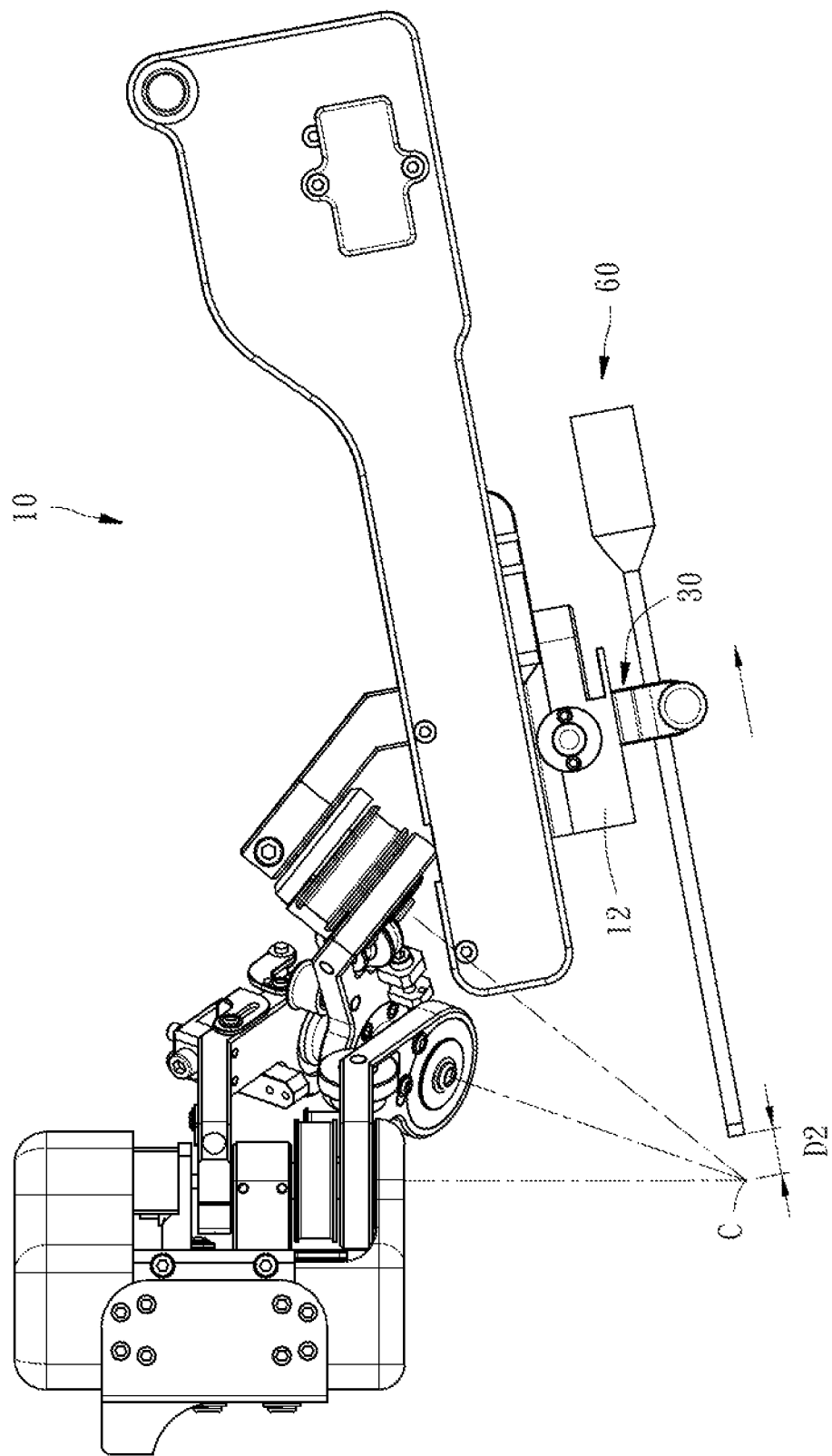
FIG. 9, similar to FIG. 6, shows the endoscope moving away from the spherical remote center of motion.
Figure 10:
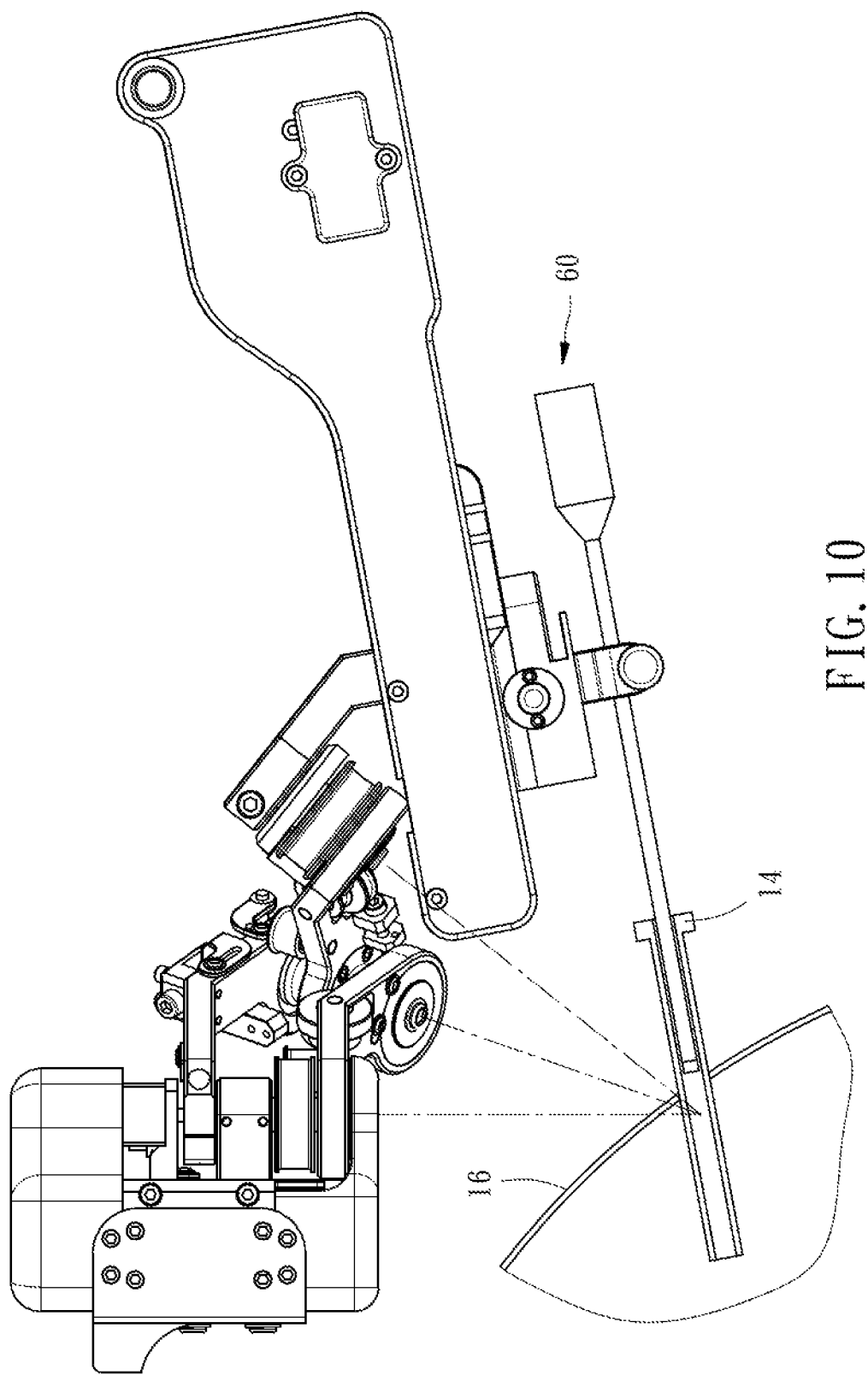
FIG. 10, similar to FIG. 9, shows the endoscope inserted into the catheter.
Figure 11:
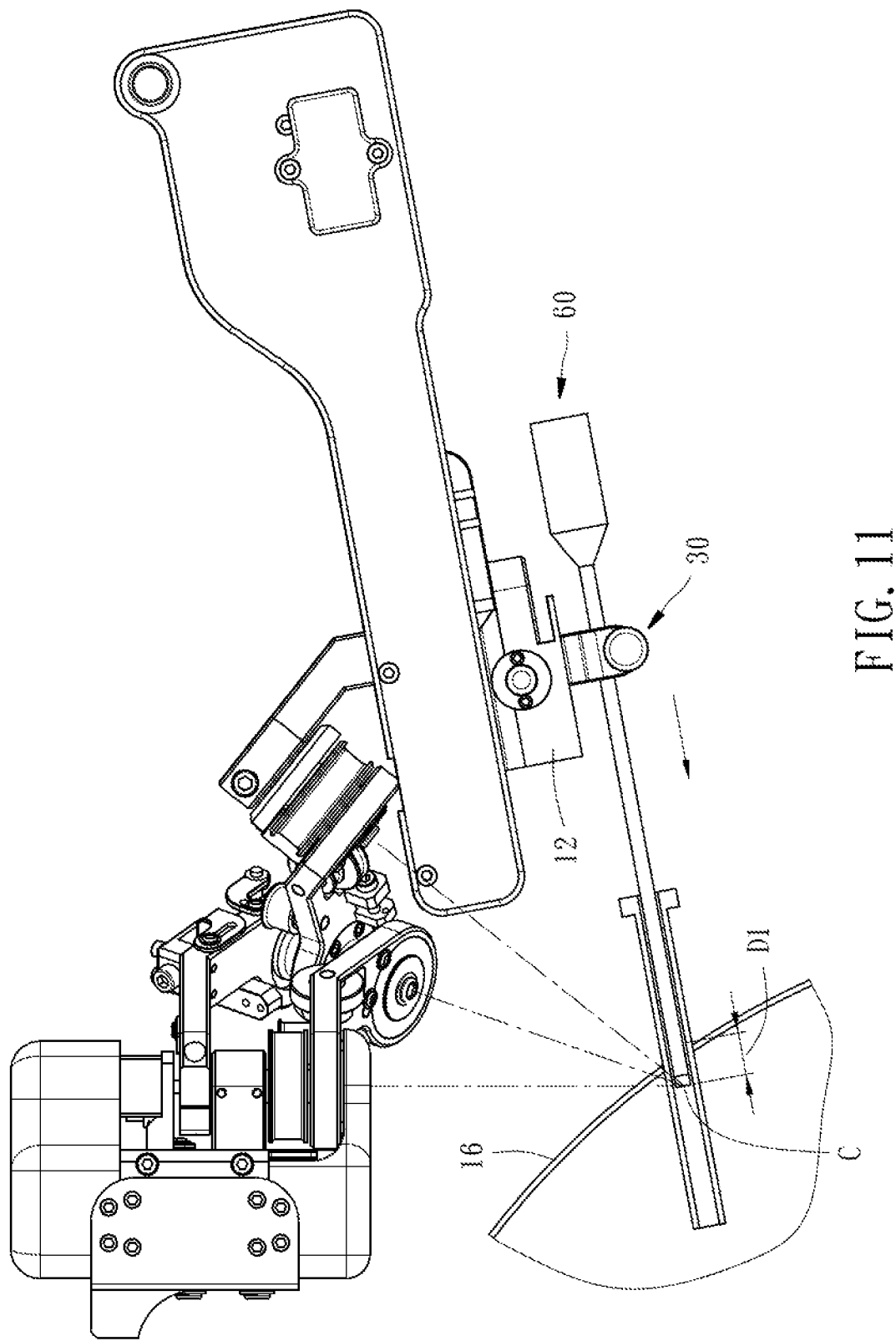
FIG. 11, similar to FIG. 10, shows the endoscope moving toward the remote center of motion.

More particularly, as shown in FIG. 8, in Step d), the first thing to do is to select a positioning depth D1 where the endoscope 60 is inserted into the body cavity 16. Then, as shown in FIG. 9, the movable seat 12 of the robot arm 10 is activated to drive the fastener 30 of the auxiliary positioning device 20, so that the fastener 30 and the endoscope 60 are driven to move away from the spherical remote center of motion C of the robot arm 10 for a predetermined distance D2. The predetermined distance D2 is equal to the positioning depth D1. Afterward, in Step e), as shown in FIG. 10, after the endoscope 60 is inserted into the catheter 14, the movable seat 12 of the robot arm 10 is activated again to drive the fastener 30 of the auxiliary positioning device 20. At last, as shown in FIG. 11, the fastener 30 and the endoscope 60 are driven to move toward the spherical remote center of motion C of the robot arm 10 for the predetermined distance D2. Thereby, the terminal of the endoscope 60 is separated from the surface of the body cavity 16 by the initially set positioning depth D1, thereby accomplishing the positioning process.

To sum up, the disclosed method can complete two works for preoperative preparation in a single action. In other words, by inserting the endoscope 60 into the catheter 14, the positioning of the endoscope 60 can be accomplished, thereby reducing time required by preoperative preparation and improving preciseness of positioning. In addition, since the entire process involves no additional tools that directly contact the patient's body cavity, the risk of infection can be significantly reduced.

What is claimed is:

1. A method for positioning an endoscope, the method comprising the following steps:
   a) installing a robot arm, wherein the robot arm defines a spherical remote center of motion;
   b) preparing an auxiliary positioning device, wherein the auxiliary positioning device has a fastener, a docking member detachably connected to the fastener, and an apparatus-receiving hole passing through the fastener and the docking member, and installing the fastener of the auxiliary positioning device onto the robot arm, so that a terminal of the docking member of the auxiliary positioning device coincides with the spherical remote center of motion of the robot arm;
   c) inserting an endoscope into the apparatus-receiving hole of the auxiliary positioning device, in a way that the endoscope is fixed to the auxiliary positioning device and a terminal of the endoscope is aligned with the terminal of the docking member of the auxiliary positioning device;
   d) removing the docking member of the auxiliary positioning device, so that the terminal of the endoscope coincide with the spherical remote center of motion of the robot arm; and e) inserting the endoscope into a catheter that has been inserted in a body cavity.

2. The method of claim 1, wherein the auxiliary positioning device further comprises a knob deposited on the fastener, and the method further comprises in the step c), when the endoscope has been inserted into the apparatus-receiving hole of the auxiliary positioning device, rotating the knob to make the fastener fix the endoscope.

3. The method of claim 1, further comprising in the step d), when the docking member of the auxiliary positioning device has been removed, turning on a light source of the endoscope.

4. The method of claim 1, further comprising in the step b), installing the fastener of the auxiliary positioning device on a movable seat of the robot arm, in the step d), selecting a positioning depth where the endoscope is inserted into the body cavity, and activating the movable seat of the robot arm to drive the fastener of the auxiliary positioning device, so that the fastener drives the endoscope to move away from the spherical remote center of motion of the robot arm for a predetermined distance, in which the predetermined distance is equal to the positioning depth, and in step e), when the endoscope has been inserted into the catheter, activating the movable seat of the robot arm again to drive the fastener of the auxiliary positioning device, so that the fastener drives the endoscope to move toward the spherical remote center of motion of the robot arm for the predetermined distance.

* * * * *